US00PP32772P3

(12) United States Plant Patent
Bentley

(10) Patent No.: US PP32,772 P3
(45) Date of Patent: Jan. 26, 2021

(54) ***ESCALLONIA* PLANT NAMED 'IB411-1'**

(50) Latin Name: ***Escallonia* hybrid**
Varietal Denomination: IB411-1

(71) Applicant: Howard Bentley, Wonga Park (AU)

(72) Inventor: Howard Bentley, Wonga Park (AU)

( * ) Notice: Subject to any disclaimer, the term of this patent is extended or adjusted under 35 U.S.C. 154(b) by 0 days.

(21) Appl. No.: 16/602,479

(22) Filed: Oct. 16, 2019

(65) Prior Publication Data

US 2020/0120846 P1 Apr. 16, 2020

(30) Foreign Application Priority Data

Oct. 16, 2018 (AU) ..... PBR 2018/307

(51) Int. Cl.
*A01H 5/02* (2018.01)
*A01H 6/00* (2018.01)

(52) U.S. Cl.
USPC ..... Plt./226
CPC ..... *A01H 6/00* (2018.05); *A01H 5/02* (2013.01)

(58) Field of Classification Search
USPC ..... Plt./226
CPC ..... A01H 6/00; A01H 5/02
See application file for complete search history.

*Primary Examiner* — Keith O. Robinson
(74) *Attorney, Agent, or Firm* — Samuel R. McCoy, Jr.

(57) ABSTRACT

A new and distinct *Escallonia* hybrid plant named 'IB411-1' which is characterized by a compact, densely-foliaged growth, relatively small foliage, mid to light pink flowers, and the stability of these characteristics from generation to generation.

2 Drawing Sheets

Latin name of the genus and species: The Latin name of the genus and species of the novel variety disclosed herein is *Escallonia* hybrid.

Variety denomination: The inventive variety of *Escallonia* hybrid disclosed herein has been given the variety denomination 'IB411-1'.

CROSS REFERENCE TO RELATED APPLICATIONS

This application claims priority to the Australian Plant Breeder's Rights application number 2018/307, filed on Oct. 16, 2018, which is herein incorporated by reference.

BACKGROUND OF THE INVENTION

Parentage: 'IB411-1' is a hybrid seedling selection resulting from the controlled pollination of *Escallonia exoniensis* 'Fradesii Nana' (not patented), the seed parent, with an unnamed, white-flowered progeny of *Escallonia* sp. 'Peach Blossom' (not patented), the pollen parent. A controlled breeding program was undertaken at the inventors' commercial plant nursery in Wonga Park, Victoria, Australia with the goal of developing a range of *Escallonia* hybrids that exhibited small foliage size, varying flower colors and densely foliaged growth habits. As part of the breeding program, controlled pollination took place in the summer of 2010-2011. Seed was collected from said cross and subsequently sown in June 2011. The resulting seedlings were grown to flowering maturity in the summer of 2012. At that time, fourteen selections were made and further grown on in the field for evaluation. Cuttings were also taken from each selection for container production trials. In February of 2015, one seedling was observed which exhibited small foliage, a compact and densely foliaged growth habit with pink flowers. The seedling was isolated for further evaluation in order to confirm the distinctness and stability of the characteristics first observed. Upon confirmation of distinctness and stability, 'IB411-1' was selected for commercialization.

Asexual Reproduction: 'IB411-1' was first asexually reproduced by way of softwood stem cuttings in the summer of 2012 at the inventor's nursery in Wonga Park, Victoria, Australia. Through seven subsequent generations, the unique features of this cultivar have proven to be stable and true to type.

SUMMARY OF THE INVENTION

The following characteristics have been repeatedly observed and represent the distinguishing characteristics of the new *Escallonia* cultivar, 'IB411-1'. These traits, in combination, distinguish 'IB411-1' as a new and distinct cultivar.

1. 'IB411-1' exhibits a short plant height and a densely-foliaged growth habit; and
2. 'IB411-1' exhibits an abundance of relatively small foliage; and
3. 'IB411-1' exhibits an abundance of mid to light pink flowers.

BOTANICAL DESCRIPTION OF THE PLANT

Figure 1:
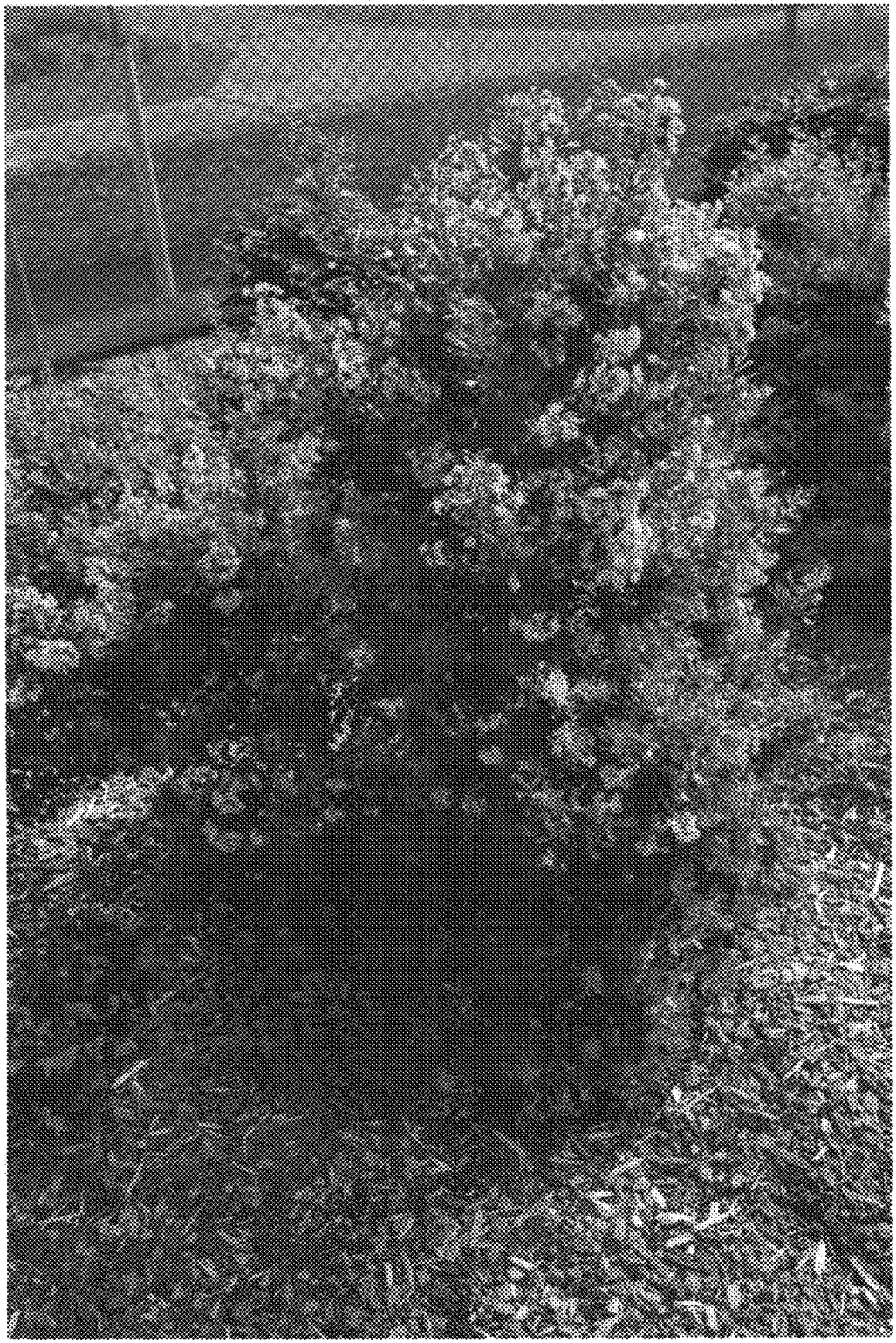
FIG. 1 illustrates, as nearly true as it is reasonably possible to make the same in color photographs of this type, an exemplary 2-year-old 'IB411-1' plant grown outdoors in Monbulk, Melbourne, Australia.
Figure 2:
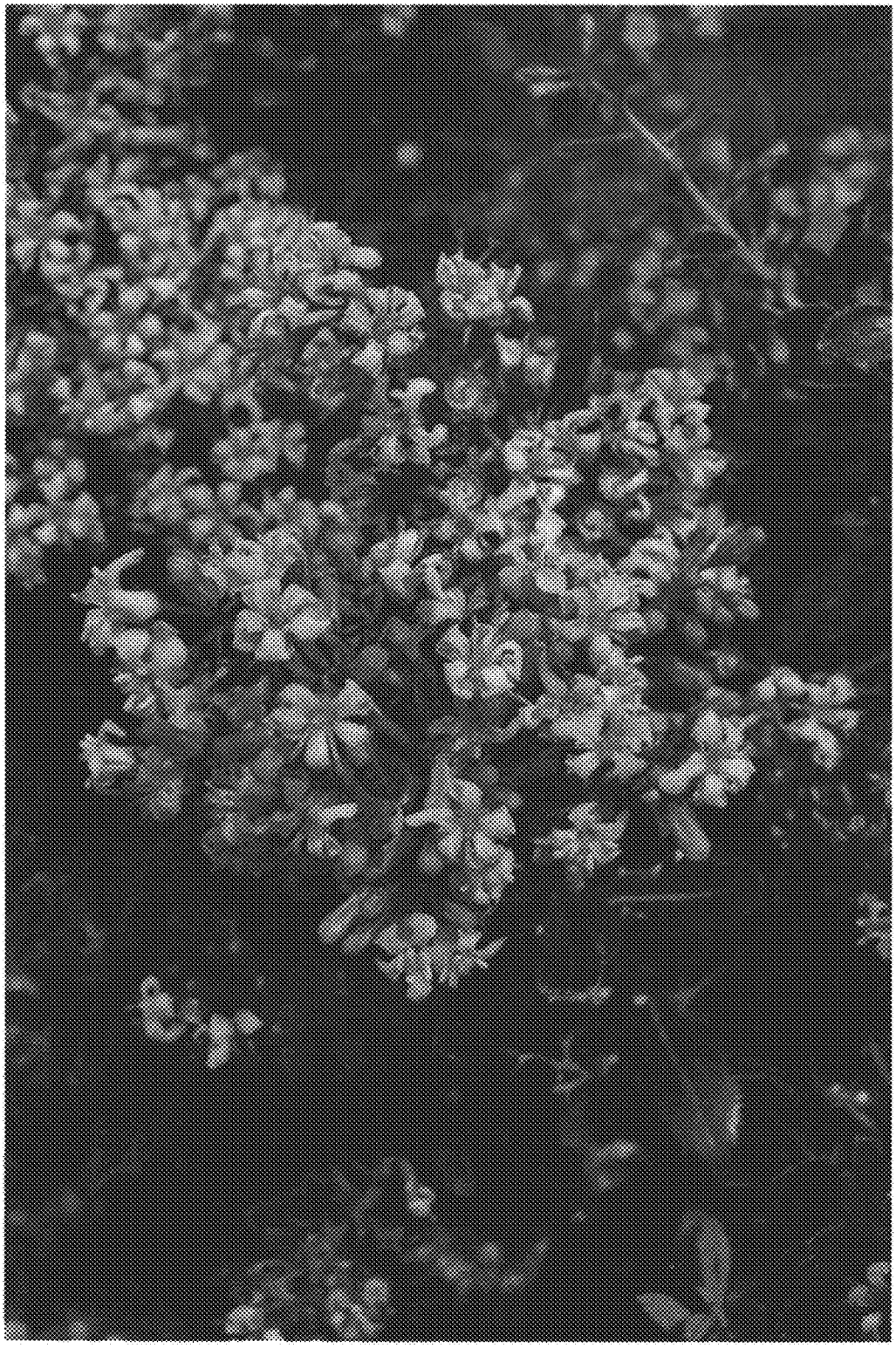
FIG. 2 illustrates, as nearly true as it is reasonably possible to make the same in color photographs of this type, exemplary inflorescence and flowers of a 2-year-old 'IB411-1' plant grown outdoors in Monbulk, Melbourne, Australia.

The following is a detailed botanical description of a new and distinct variety of a *Escallonia* hybrid plant known as 'IB411-1'. Plant observations were made on plants grown in Wonga Park, Victoria, Australia. Unless indicated otherwise, the descriptions disclosed herein are based upon observations made from 1 year old 'IB411-1' plants grown outdoors in 2 liter nursery containers. Plants were grown under full sun exposure, fertilized with a slow release granular fertilizer product, and were regularly watered with overhead irrigation. Temperatures ranged between 13 and 28 degrees Celsius during the day and 3 to 11 degrees Celsius at night. No pest and disease measures were taken. Observation data were recorded in October of 2019.

Those skilled in the art will appreciate that certain characteristics will vary with older or, conversely, younger plants. 'IB411-1' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart*, The Royal Horticultural Society, London, 1986 edition except where common terms of color are used.

A botanical description of 'IB411-1' and comparisons with the parent plants and closest known comparator are provided below.

General plant description:

*Plant type*.—Evergreen perennial shrub.

*Growth habit*.—Compact mounding habit.

*Height*.—Approximately 1.0 meter at maturity; 20 cm as observed.

*Width*.—Approximately 1.4 meter at maturity; 30 cm as observed.

*Plant vigor*.—Moderately vigorous.

*Hardiness*.—USDA Zone 7.

*Pest and disease susceptibility or resistance*.—Not any more or less tolerant or susceptible to pests or diseases known to effect *Escallonia* sp. such as fungal leaf spot (*Mycosphaerella* sp.), oak root fungus (*Armillaria mellea*), Chinese wax scale (*Ericerus pela*), and two-spotted mite (*Tetranychus urticae*).

*Propagation*.—Propagation method — Softwood stem cuttings. Time to develop roots — 4 to 5 weeks. Crop time — From 8 to 10 weeks are needed to produce a fully rooted cutting and 30 weeks to produce a marketable plant in a 140 mm nursery pot, depending on geographic location.

Root system:

*General*.—Fibrous; freely branched and moderately dense rooting.

*Distribution in the soil profile*.—Shallow to moderately deep.

*Texture*.—Juvenile roots are fleshy; older roots are woody.

Stems:

*Branching habit*.—One main stem, itself freely branching, and giving rise to numerous lateral branches. Lateral branches arising from as low as soil level which, as the plant reaches maturity, results in a multi-stemmed plant.

*Main stem*.—Attitude — Upward and outward. Aspect — Rounded. Strength — Weak to medium strength. Diameter — 10 mm at the base. Texture — Glabrous. Luster — Slightly glossy. Color — Yellow-green, nearest to RHS 145B. Color, oldest wood — Greyed-orange, RHS 175D.

*Lateral branches*.—Quantity — 8. Attitude — Upward and outward; angle to main stems varying between 30 and 65 degrees. Aspect — Rounded with shallow axial ribs. Strength — Strong. Dimensions — 20 cm long and 5 mm in diameter. Internode length — 6 mm. Texture — Moderately glandular. Luster — Slightly glossy. Color — Yellow-green, nearest to in between RHS 144A and 146D.

Foliage:

*Arrangement*.—Alternate.

*Attachment*.—Petiolate.

*Division*.—Simple.

*Shape*.—Elliptic.

*Dimensions*.—2.8 cm long and 1.2 cm wide.

*Apex*.—Obtuse.

*Base*.—Attenuate.

*Margin*.—Serrulate.

*Texture, adaxial and abaxial surfaces*.—Smooth; glabrous.

*Luster, adaxial and abaxial surfaces*.—Glossy.

*Fragrance*.—No discernable fragrance.

*Color*.—Juvenile foliage, adaxial surface — Yellow-green, nearest to RHS 144A. Juvenile foliage, abaxial surface — Yellow-green, nearest to RHS 144A. Mature foliage, adaxial surface — Green, nearest to in between RHS 137A and 139A. Mature foliage, abaxial surface — Green, nearest to in between RHS 137A and 139A.

*Venation*.—Pattern — Pinnate. Vein color, adaxial surface — Midrib is yellow-green, RHS 144A; all other veins are colored the same as the surrounding foliage. Vein color, abaxial surface — Midrib is yellow-green, RHS 144A; all other veins are colored the same as the surrounding foliage.

*Petiole*.—Dimensions — 5.0 mm long and 1.5 mm in diameter. Aspect — Round. Strength — Moderately strong. Texture — Smooth; glabrous. Luster — Very slightly glossy. Color — Yellow-green, nearest to RHS 144A.

*Stipules*.—None present.

Inflorescence:

*Type*.—Terminal panicle.

*Natural flowering season*.—From late spring into mid-summer in Wonga Park, Victoria, Australia.

*Quantity of flowers per inflorescence*.—55.

*Panicle dimensions*.—5.0 cm long and 4.8 cm wide.

*Peduncle*.—Dimensions — 4.3 cm long and 0.2 cm in diameter. Attitude — Near horizontal. Aspect — Generally round and shallowly axially ribbed. Strength — Strong. Texture — Densely glandular. Luster — Slightly glossy. Color — Yellow-green, nearest to a mixture of RHS 146D, 151A, 153A, and 153B; becoming progressively suffused with greyed-red, nearest to RHS 178A, distally.

Bud:

*Dimensions*.—Approximately 9 mm long and 3 mm in diameter.

*Shape*.—Narrow obovate.

*Texture*.—Smooth; glabrous.

*Luster*.—Very slightly glossy.

*Color*.—Red-purple, nearest to a combination of RHS 57A, 57B, 57C and 57D.

Flower:

*General description*.—Zygomorphic, tubular flower comprised of a corolla tube and four dorsal petal lobes and one longer ventral lobe. Solitary flowers occurring within the foliage.

*Lastingness*.—5 days.

*Persistence*.—Self-cleaning.

*Fragrance*.—Not fragrant.

*Attitude*.—Upright and outward.

*Pedicels*.—Attitude, relative to peduncle — Semi-erect; approximately 45 degrees. Aspect — Round. Dimensions — 4 mm long and 1 mm in diameter. Texture — Smooth; glabrous. Luster — Matte. Strength — Moderately strong. Color — Yellow-green, nearest to a mixture of RHS 146D, 151A, 153A, and 153B; heavily suffused with greyed-red, nearest to RHS 178A.

*Calyx*.—Quantity of sepals — 5 fused sepals. Arrangement — Fused into a lobed tube. Sepals — Sepal lobe dimensions — 6 mm long and 3 mm wide. Sepal lobe shape — Broad elliptic. Sepal lobe apex — Broad acuminate. Sepal lobe margin — Entire. Texture, inner surface — Moderately glandular. Texture, outer surface — Glabrous. Luster, inner surface — Slightly glossy. Luster, outer surface — Slightly glossy. Color when fully open, inner surface — Yellow-green, nearest to a mixture of RHS 146D, 151A, 153A, and 153B; heavily suffused with greyed-red, nearest to RHS 178A. Color when fully open, outer surface — Yellow-green, nearest to a mixture of RHS 146D, 151A, 153A, and 153B; heavily suffused with greyed-red, nearest to RHS 178A.

*Corolla*.—Quantity of petals — Five. Arrangement — Rotate; petals are unfused. Dimensions — 12 mm deep and 14 mm in diameter. Petals — Shape — Narrowly obovate. Dimensions — 15 mm long and 4 mm wide. Aspect — Heavily reflexed. Apex — Obtuse. Base — Narrow cuneate. Margin — Entire; moderately undulated. Texture, inner and outer surfaces — Smooth; glabrous. Luster, inner and outer surfaces — Matte. Color when opening, inner surface — White, RHS 155D, and becoming progressively suffused with red-purple, nearest to a combination of RHS 57A and 57B, towards the margins and apex. Color when opening, outer surface — White, RHS 155D, and becoming progressively suffused with red-purple, nearest to a combination of RHS 57A and 57B, towards the margins and apex. Color when fully open, inner surface — White, RHS 155D, and moderately to heavily suffused with red-purple, nearest to a combination of RHS 58B and 58C. Color when fully open, outer surface — White, RHS 155D, and moderately to heavily suffused with red-purple, nearest to a combination of RHS 58B and 58C. Petal color fading to — White, RHS 155D, and lightly suffused with red-purple, nearest to RHS 58D.

Reproductive organs:

*Androecium*.—Stamens — Quantity — 5. Position — Superior to the corolla and inferior to the pistil. Overall length — 9 mm long. Filament — Dimensions — 8 mm long and 0.5 mm in diameter. Color — White, RHS 155D, and moderately to heavily suffused with red-purple, nearest to RHS 58C. Anthers — Shape — Oblong, with two anther sacs. Diameter — 1.5 mm in diameter and 2.5 mm long. Color — Greyed-yellow, nearest to RHS 160A. Pollen — Abundant. Pollen Color — Yellow, nearest to RHS 11A.

*Gynoecium*.—Pistils — Quantity — 1. Stigma — Shape — Club-shaped. Dimensions — Approximately 1 mm long and 1 mm in diameter. Color — Yellow-green, nearest to RHS 144B. Style — Aspect — Rounded. Attitude — Slightly curved towards the distal end. Dimensions — 8 mm long and 0.75 mm wide. Color — Greyed-yellow, nearest to RHS 161B. Ovary — Position — Superior. Color — Yellow-green, nearest to RHS 151A.

Fruit and seed: None observed.

COMPARISONS WITH THE PARENT PLANTS

Plants of the new cultivar 'IB411-1' differ from the seed parent, *Escallonia exoniensis* 'Fradesii Nana' (not patented), in the following characteristics described in Table 1 below.

TABLE 1

| Characteristic | 'IB411-1' | 'Fradesii Nana' |
|---|---|---|
| Plant height. | Taller than 'Fradesii Nana'. | Shorter than 'IB411-1'. |
| General coloration of the flower. | Mid to light pink. | Dark red. |

Plants of the new cultivar 'IB411-1' differ from the pollen parent, an unnamed white-flowered progeny of *Escallonia* sp. 'Peach Blossom' (not patented), in the following characteristics described in Table 2 below.

TABLE 2

| Characteristic | 'IB411-1' | Pollen parent. |
|---|---|---|
| Growth habit. | More densely foliaged. | Less densely foliage. |
| Plant height. | Shorter than the pollen parent. | Taller than 'IB411-1'. |
| General coloration of the mature foliage. | A darker shade of green, relative to the pollen parent. | A lighter shade of green, relative to 'IB411-1' |
| General coloration of the flower. | Mid to light pink. | White. |

COMPARISONS WITH THE CLOSEST KNOWN COMPARATOR

Plants of the new cultivar 'IB411-1' differ from the closest known commercial comparator, *Escallonia* sp. 'Peach Blossom' (not patented), in the following characteristics described in Table 3 below.

TABLE 3

| Characteristic | 'IB411-1' | 'Peach Blossom' |
|---|---|---|
| Growth habit. | More densely foliaged. | Less densely foliage. |
| Plant height. | Shorter than 'Peach Blossom'. | Taller than 'IB411-1'. |
| General coloration of the mature foliage. | A darker shade of green, relative to the pollen parent. | A lighter shade of green, relative to 'IB411-1'. |

That which is claimed is:

1. A new and distinct variety of *Escallonia* hybrid plant named 'IB411-1', substantially as described and illustrated herein.

* * * * *